Figure 1:
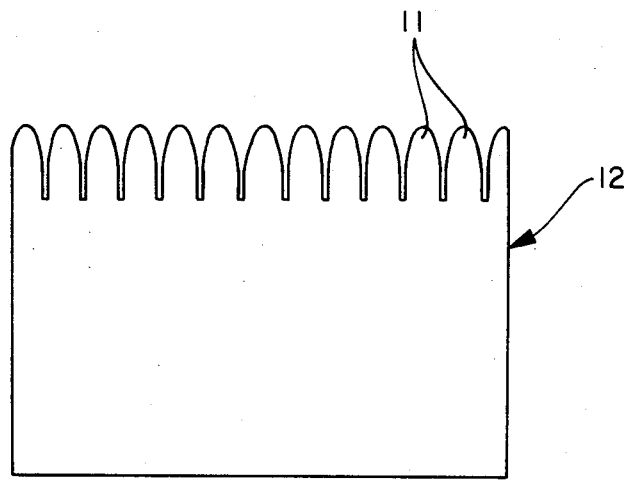

United States Patent [19]

Johnson

[11] Patent Number: 4,543,086
[45] Date of Patent: Sep. 24, 1985

[54] COMPACT TAMPON APPLICATOR

[75] Inventor: Carl W. Johnson, Winnebago County, Wis.

[73] Assignee: Kimberly-Clark Corporation, Neenah, Wis.

[21] Appl. No.: 616,043

[22] Filed: Jun. 1, 1984

[51] Int. Cl.⁴ ............................................. A61F 15/00
[52] U.S. Cl. ...................................... 604/11; 604/15; 604/904
[58] Field of Search ...................... 604/14, 16, 15, 11, 604/12, 13, 18, 17, 904

[56] References Cited

U.S. PATENT DOCUMENTS 3,765,416 10/1973 Weoner ................................. 604/18
4,148,317 4/1979 Loyer ................................... 604/11
4,198,978 4/1980 Nigro ................................... 604/15

Primary Examiner—John D. Yasko
Assistant Examiner—Christa K. Scott

[57] ABSTRACT

A compact tampon applicator is provided with telescoping inner and outer tubes. The inner tube has a slot with a stop at the upper and lower end and an opposite positioned slot having a stop only at the lower end. A bridge traversing the diameter of the outer tube on an angle is provided which supports the tampon pledget and also provides guiding and stop means for the inner tube as it is first withdrawn to push against and expel the pledget.

2 Claims, 5 Drawing Figures

COMPACT TAMPON APPLICATOR

FIELD OF THE INVENTION

This invention relates to a tampon tube applicator and particularly a tampon tube applicator having telescoping inner and outer tubes.

BACKGROUND OF THE INVENTION

Tampon tube applicators are used as means to aid in the insertion of tampon pledgets. These applicators generally include an outside tube usually with petal-like projections which are formed to provide a bullet-shaped leading or insertion end as well as a cooperating, inner tube. The inner tube slides between the outer tube and tampon pledget and during insertion is used as a plunger to push the tampon pledget through the leading end of the outer tube and into its proper position within the vagina. Telescoping tubes in which the tubes nest and length of the inner and outer tube are approximately the same are popular because of the desire for compactness and discreteness in the transportation and use of tampons.

Examples of some of the compact tampon tubes can be found in U.S. Pat. Nos. 4,276,881, 3,101,713 and 4,291,696 and Canadian Pat. No. 700,840. Each of the U.S. patents mentioned above utilizes the dual telescoping tube principle and employs means for reducing the inner tube diameter at its leading end as it is withdrawn and used as a plunger during insertion.

There is also means positioned near the rear of the outer tube for preventing the tampon from falling out. This may be in the form of a ring or a series of inward projections. Since these tubes are often made of thermoplastic material and therefore must be injection molded, the molding of the inside of the outer tube when other than a smooth surface is required, is difficult and expensive.

In addition, each of these tubes requires some form of guiding means usually positioned to slide in mating slots in the inner tube. These guiding means are generally in the form of inward projections disposed around the inside surface of the outer tube. The same problem with regard to difficulty of manufacture also is inherent in these guide means.

SUMMARY OF THE INVENTION

According to this invention, a compact tampon applicator is made in which a bridge diagonally spanning the inner diameter of the telescoping tubes forms both a stop for the tampon pledget and also guiding means for slots positioned in the inner tube to allow for withdrawal and plunger expulsion during insertion.

DESCRIPTION OF THE INVENTION AND DRAWINGS

Figure 2:
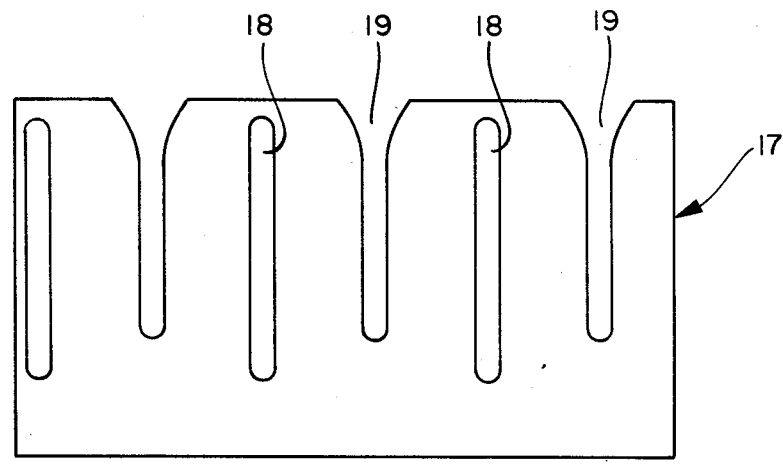
Figure 3:
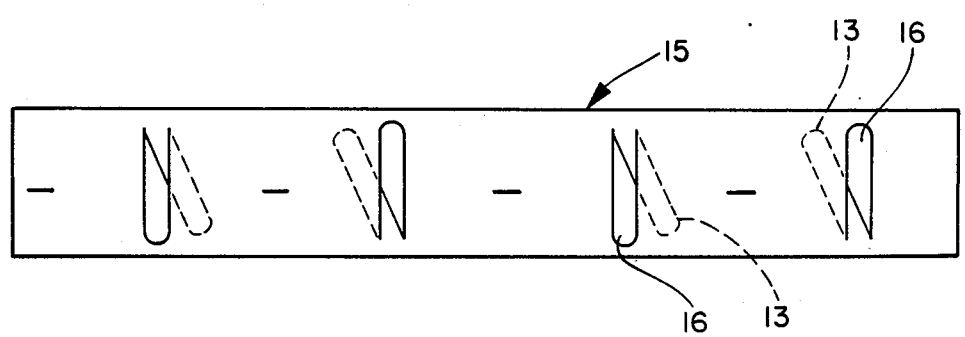
Figure 4:
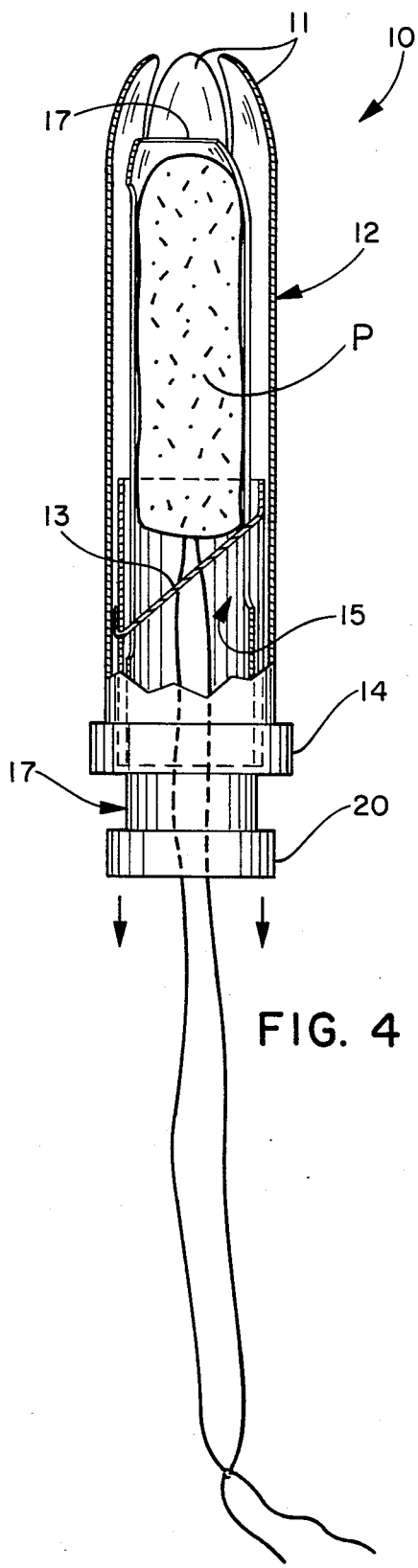
Figure 5:
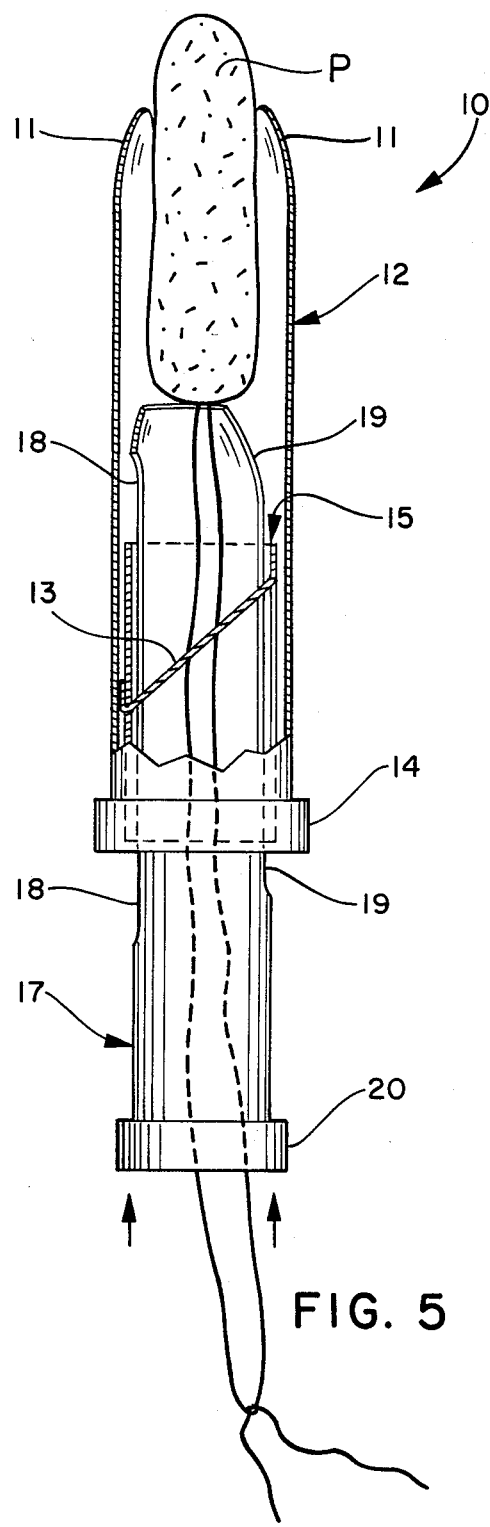

The invention may be more readily understood by reference to the drawings in which:

FIGS. 1, 2 and 3 are plan views of the inner tube, outer tube and mating sleeve blanks, respectively; and FIGS. 4 and 5 are views of the assembled tampon tube and pledget with FIG. 5 showing the tampon pledget partially expelled.

An outer tampon tube blank as depicted in FIG. 1 is shown in which a plurality of lobes or petals 11 are cut in otherwise essentially rectangular blank 12.

If the tube blank is made of paper, it can either be cylindrically butted and sealed or else convolutely wound so that the petals overlap and then thermally bonded or adhesively sealed to form the cylindrical outer tube. The ends of the petals are curved and folded inward by techniques such as post-forming or heat setting a paper tube having a plastic coating. These techniques are well known in the tampon tube art.

An inner tube blank 17, as depicted in FIG. 2 shows a closed slot 18 having a stop near the leading and rear portions of the tube and an open slot 19 having no stop at the leading portion and only a single stop at the rear portion of the tube blank which does not extend as far towards the rear portion as the closed slot stop 18. When the inner tube is formed, the slot 18 is directly opposite the slot 19. The inner tube 17 is formed in the same manner as the outer tube. Both the blanks depicted in FIGS. 1 and 2 can of course be injection molded easily due to their simple profile if they are made of thermoplastic material. When the inner tube is formed, the slot 18 is directly opposite the slot 19.

In a currently preferred embodiment of this invention, as shown in FIG. 3, an inner sleeve 15 is formed and, as can be seen by reference to FIGS. 4 and 5, is positioned between the inner and outer tube. Bridge members 13 are cut to form opposite ends of openings 16. The sleeve is then formed. The bridge portions 13 which are longer than the diameter of the sleeve overlap at the center to form a diagonal span which is adhesively secured at the overlap and attached to and formed from sleeve 15.

Referring to FIG. 4, the pledget P of the tampon rests upon the leading edge of the bridge 13 the inner sleeve 15 while the inner tube 17 partially surrounds and is coextensive with tampon pledget P. Slot 19 of the inner tube 17 is engaged by the leading edge of the bridge 13 while the closed slot 18 is positioned to engage the trailing edge of the bridge 13. Preferably a finger grip 14 is provided the outer tube for ease of handling and an outer ring 20 is attached to the inner tube 17 to prevent its total entry into the inner tube during tampon expulsion.

As can be seen in FIG. 5, the inner tube 17 has been completely withdrawn and is in the process of being pushed forward to expel the tampon pledget P.

As mentioned above, the embodiment utilizing the sleeve is currently preferred for aesthetic purposes although a simpler embodiment is possible. In the simpler embodiment, the bridge member is cut from the outer tube rather than in a separate sleeve member. The bridge member is positioned and attached in the same way to the opposite side of the outer tube as was the case when the bridge member spanned the sleeve.

I claim:

1. A tampon applicator comprising in combination
    (a) an outer tube with an insertion end;
    (b) a bridge member diagonally spanning the inner diameter of the outer tube;
    (c) an inner tube with a first slot and a second slot disposed opposite said first slot;
    (d) said first slot extending from a first stop near said tube base to a second stop near the opposite end of said base;
    (e) said second slot extending from said opposite end to another stop near said base but farther from said base than said first stop said second stop and said another stop simultaneously in contact with said bridge when the tube is expelled the side of said bridge member nearest the end engaging said second slot; and (f) an outer shoulder extending around said inner tube base to prevent the inner tube base from entering the outer tube.

2. The applicator according to claim 1 wherein the opening at the opposite end of the second slot is wider than at the area near said another slot.

* * * * *